(12) United States Patent
Bailey et al.

(10) Patent No.: US 6,891,381 B2
(45) Date of Patent: May 10, 2005

(54) HUMAN BODY: SCANNING, TYPING AND PROFILING SYSTEM

(75) Inventors: Kenneth S Bailey, Satellite Beach, FL (US); Fernando A Barrera, West Hills, CA (US)

(73) Assignee: Secure Logistix, Newport Beach, CA (US)

( * ) Notice: Subject to any disclaimer, the term of this patent is extended or adjusted under 35 U.S.C. 154(b) by 691 days.

(21) Appl. No.: 09/751,208

(22) Filed: Dec. 29, 2000

(65) Prior Publication Data

US 2004/0012398 A1 Jan. 22, 2004

Related U.S. Application Data

(60) Provisional application No. 60/174,061, filed on Dec. 30, 1999.

(51) Int. Cl.[7] ............................................. G01R 27/04
(52) U.S. Cl. ...................... 324/644; 324/642; 702/159
(58) Field of Search ......................... 324/609, 637–644, 324/658, 663; 340/516, 568.1; 702/167, 159; 342/25 R, 46

(56) References Cited

U.S. PATENT DOCUMENTS

| | | | | |
|---|---|---|---|---|
| 3,490,037 A | * | 1/1970 | Williams | 324/644 |
| 3,691,557 A | * | 9/1972 | Constant et al. | 342/25 |
| 3,801,978 A | * | 4/1974 | Gershberg et al. | 340/516 |
| 4,773,029 A | * | 9/1988 | Claesson et al. | 702/167 |
| 4,975,968 A | * | 12/1990 | Yukl | 382/100 |
| 5,578,933 A | * | 11/1996 | Nonaka | 324/639 |
| 6,057,761 A | * | 5/2000 | Yukl | 340/568.1 |
| 6,664,916 B1 | * | 12/2003 | Stafford et al. | 342/46 |

* cited by examiner

Primary Examiner—Vincent Q. Nguyen
(74) Attorney, Agent, or Firm—Fish & Richardson P.C.

(57) ABSTRACT

A body scanning measurement, typing and profiling apparatus and method utilizing microwave energy. Microwaves are used to measure the size and shape of an individual. An array of miniaturized transmitting antennas direct RF energy to a similarly sized array of receiving antennas. Microwaves are directed toward an object, such as a human being, to be measured and the unabsorbed energy of the microwaves transmitted is measured and converted to a signal representative of the size and shape of the object being measured. A computer processor generates vital body measurements and stores such measurements for future use.

9 Claims, 10 Drawing Sheets

CATEGORY 1: VITALS

```
BODY TYPE: STICK
HEIGHT: 6'4"
HEAD SIZE: 7 1/4"
NECK: 17"
CHEST: 45"
WAIST: 34"
HIPS: 41"
INSEAM: 38"
SLEEVE: 37"
```

61

CATEGORY 2: PROFILE

```
BODY FAT RATIO: 7%
TORSO: 3:5
LEG: 7:9
ARM: 8:10
HAND: 11:13
FOOT: 11:5
FACE: 3:4
RATING: 7:5:9
PROFILE NO.: J11-68-4QY-1
```

BODY TYPES

PEAR

WEDGE

HOUR GLASS

STICK

HUMAN BODY: SCANNING, TYPING AND PROFILING SYSTEM

RELATED APPLICATION

This application claims the benefit of U.S. Provisional Patent Application Ser. No. 60/174,061 filed Dec. 30, 1999.

BACKGROUND OF THE INVENTION

1. Field of the Invention

The present invention relates generally to the field of imaging systems. More particularly, the present invention relates to an apparatus and system for imaging a human body for the purpose of identification or body measurement for use in a plurality of consumer markets including apparel and furniture design.

2. Background of the Prior Art

For a number of years human beings have been typed by body weight, body shape, dimensions and even skin color and type. It is known that genetically human beings are nearly 95% similar. Pronounced and individualistic traits have been stored and catalogued for many years, such as fingerprints, footprints, and eye scans. More recently palm prints, wrist veins, and voice prints are all used for individual identification and recognition systems. The shape, size, and contour of other body parts could be found to be just as individualistic as fingerprints and palm prints. The exact size, shape, contour and finite dimensions of a human ear or contour of a nose, or curvature of the forehead could be utilized for positively identifying an individual human being one from another, especially if several body parts are measured, catalogued and stored and then compared as a group for purposes of positively identifying that individual at a later date. In fact, the authentication process of positively identifying someone could be effectively performed from some distance, and without physical contact, such as may be required in the case of fingerprints or an eye scan.

In recent years, the popularization of the Internet has spawned a new form of retailing and advertising such that the term "virtual" has been used in common practice to describe a "book store," "drug store," or "clothing store." A recent invention entitled "Touch and Feel" discloses a method to examine a book on the Internet, the same way one would browse a few pages of a book in a physical real world bookstore, to establish one's interest in purchasing that book. Nearly every possible product or good known to man is offered for sale today on the Internet, either by retail merchants or via Internet auctions.

Clothing goods can be colorfully shown and offered for sale on the Internet from merchants around the world, such as silk suits from Asia, Italian shoes from Italy, French fashion from Paris or suits and dresses offered by top retailers in the U.S. to foreigners around the globe. Understandably, a buyer of clothing on the Internet might be reluctant to purchase goods made overseas, even at a very attractive price, due to the likelihood that clothing purchased via the Internet may not fit properly. This fear could be allayed if the buyer had ample statistical information catalogued about their individual body type, size, build, and measurements to pass to the clothing merchant via the Internet. Given enough information, a merchant could absolutely guarantee a perfect fit of the garment, as if the buyer had stopped over to their store for a fitting in Hong Kong, for example. The present invention provides the necessary data for a perfect fit.

SUMMARY OF THE INVENTION

It is an object of the present invention to enable a device including a biometric scanner for determining characteristics of a human body.

It is another object to enable a computer system capable of determining human body measurements. A related object is to enable a computer system display for displaying human body measurements. A further related object is to enable a computer system that translates such human body measurements into designated apparel sizes.

Yet another object of the present invention is to provide a network system enabling ease of access by a user to scanned information. A related object is to enable Internet access to scanned information for application to domestic and foreign apparel manufacturers.

It is a further object of the invention to enable a device that utilizes a novel method of body measurement for identification purposes. A related object is to enable a device that utilizes a novel method of identification for verifying the identity of an individual. A related object is to enable a device that utilizes a novel method of identification for controlling access to restricted areas.

It is a further object of the invention to enable an identification system and method that permits rapid identification of individuals.

The above-listed objects are met or exceeded by the present method of providing a body scanning, typing and profiling system. In a preferred embodiment, the invention relates to a scanning device tailored to determine a user's body measurements. In an alternate embodiment, a scanning device according to the present invention can be used for the purpose of positively identifying an individual to control access to restricted areas.

Manufacturers of seats, couches, sofas, and beds could benefit their customers by knowing the exacting dimensions of a particular customer's torso. Automobile manufacturers could gain new insight into passenger comfort design, previously unknown. If thousands of various individuals were scanned and catalogued worldwide, then, using data detailed by group, age, or nationality, manufacturers could create a perfect fit for each customer. In an embodiment, a system consistent with the present invention includes a readily accessible body scanner. Preferably, a user of such scanner is provided an access code to remotely retrieve scanned information, such as through a PC computer at home. Once the data is retrieved, a user may then relay such data to any selected merchandise provider around the world. As such, a user of the system is virtually guaranteed a product with a perfect fit.

The present invention is therefore directed to the problem of developing a system for determining an individuals body measurements and structure type without requiring invasive procedures or physical interaction by the individual. The present invention also permits one to communicate such measurements to a knowledgeable recipient for use in developing apparel, furniture, physical fitness equipment and the like.

BRIEF DESCRIPTION OF THE DRAWINGS

The above and other features, aspects, and advantages of the present invention are considered in more detail, in relation to the following description of embodiments thereof shown in the accompanying drawings, in which:

FIG. 6 is a table illustration of data obtained and stored by an embodiment of the invention;

DETAILED DESCRIPTION OF THE INVENTION

The invention summarized above and defined by the enumerated claims may be better understood by referring to the following detailed description, which should be read in conjunction with the accompanying drawings in which like reference numbers are used for like parts. This detailed description of an embodiment, set out below to enable one to build and use an implementation of the invention, is not intended to limit the enumerated claims, but to serve as a particular example thereof. Those skilled in the art should appreciate that they may readily use the conception and specific embodiment disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
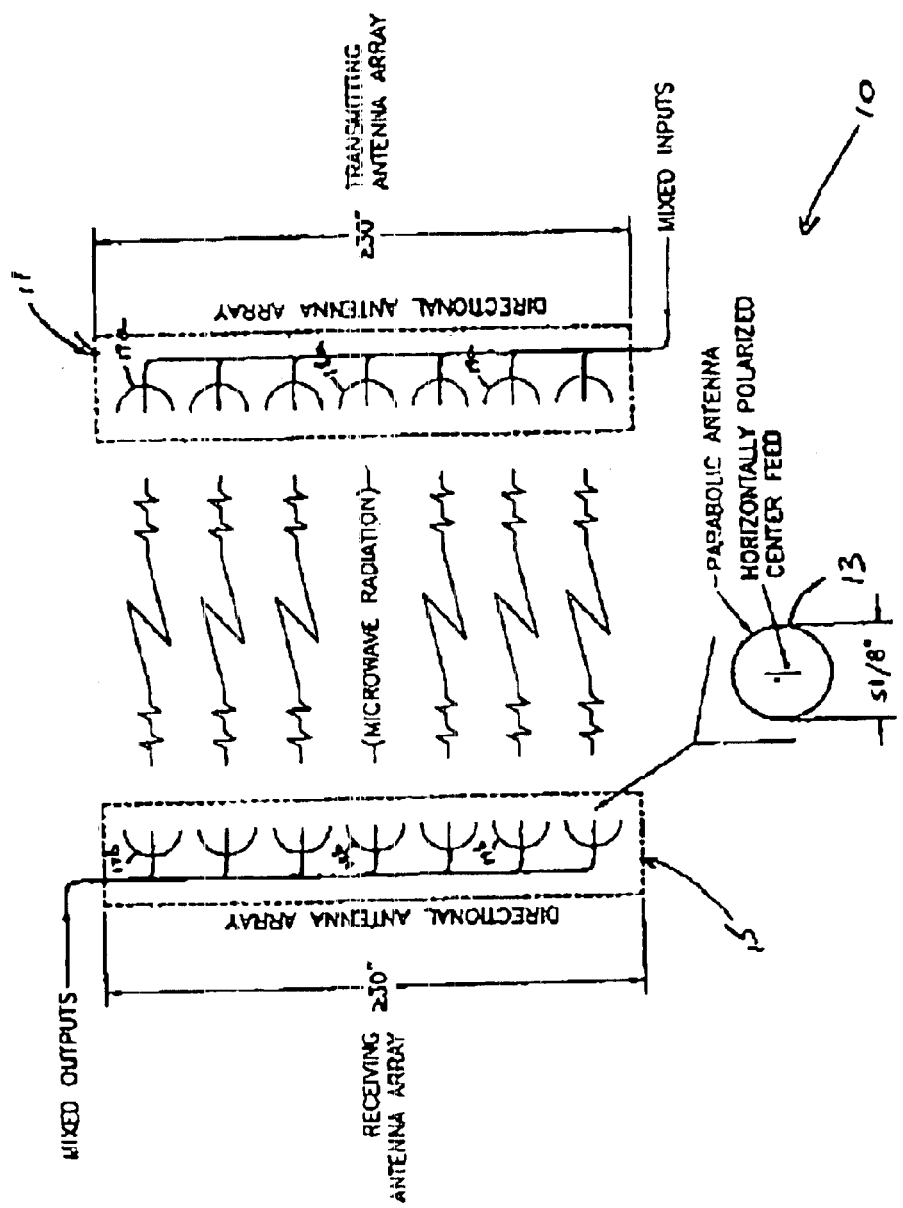
FIG. 1 is a schematic representation of transmitting and receiving antenna arrays according to the present invention.

Referring to FIG. 1, a scanner 10 comprising directional transmitting antenna array 11 and directional receiving antenna array 15 is provided. Transmitting antenna array 11 presents a linear configuration, sized approximately 30 inches long presenting a plurality of parabolic antennas, such as antenna 13. Each antenna 13 should be a miniature parabolic type antenna smaller than approximately ⅛ inch, presenting a horizontally polarized center feed. Transmitting antenna array 11 may contain approximately 240 or more parabolic antennas, such as antenna 13 disposed linearly in transmitting antenna array 11. A directional receiving antenna array 15 in linear configuration, similarly sized as transmitting antenna array 11 and presenting a plurality of parabolic antennas, such as antenna 13, is positioned to receive directed electromagnetic radiation, such as microwave radiation, transmitted from transmitting antenna array 11. Each parabolic antenna in transmitting antenna array 11 transmits to a designated parabolic antenna in receiving antenna array 15. For example, transmitting antenna 17a transmits to receiving antenna 17b; transmitting antenna 18a transmits to receiving antenna 18b; transmitting antenna 19a transmits to receiving antenna 19b, and so forth.

Figure 2:
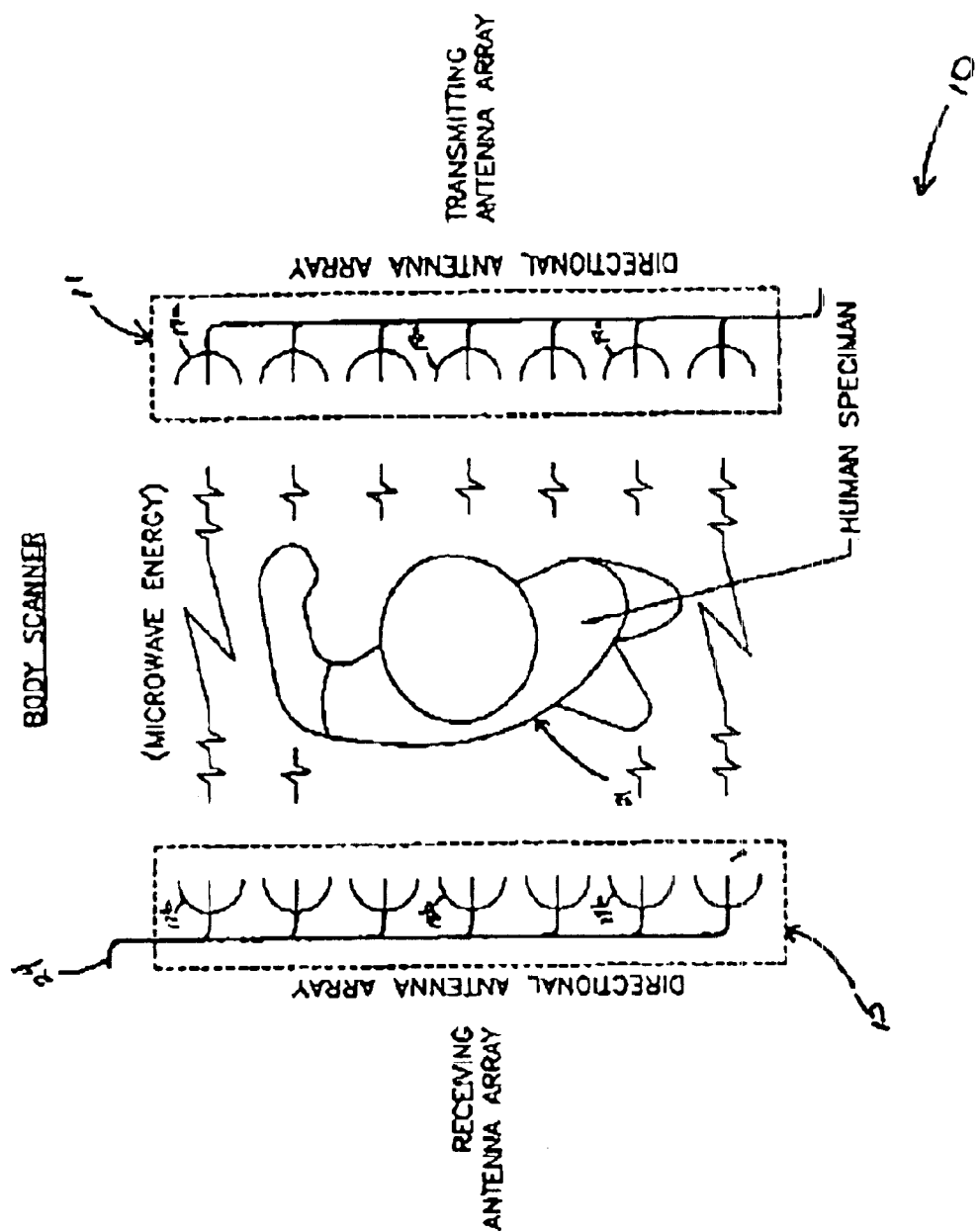
FIG. 2 is a plan view representation of horizontally oriented transmitting and receiving antenna arrays, for describing operational features of one embodiment of the present invention.

Referring now to a specific embodiment, FIG. 2 presents an illustration of a human specimen 21 undergoing a body scan utilizing the scanner apparatus 10 of the present invention. Transmitting antenna array 11 directs ultra-high frequency, low power microwave energy toward receiving antenna array 15. Not all energy transmitted from transmitting array 11 is received by receiving array 15 because the human specimen 21 blocks the path of transmission from some antennas. As illustrated, the energy transmitted from transmitting antenna 17a is received by receiving antenna 17b, but the energy transmitted from transmitting antenna 18a is blocked by the human specimen 21 and is therefore not received by receiving antenna 18b. Energy transmitted from transmitting antenna 19a may be attenuated when received by receiving antenna 19b. Such attenuation may occur due to passage of such microwave energy through clothing and the like.

The output 24 of receiving array 15 is directed to a computer system that determines which antennas of such plurality of antennas, such as antenna 13 (FIG. 1) in receiving array 15 receive energy from their corresponding transmitting antennas. Transmitting antenna array 11 is moved vertically along the entire height of the human specimen 21 substantially simultaneously with receiving antenna array 15 to scan the entire body of the human specimen 21. Such computer system can develop a two-dimensional image of the human specimen 21.

Figure 3:
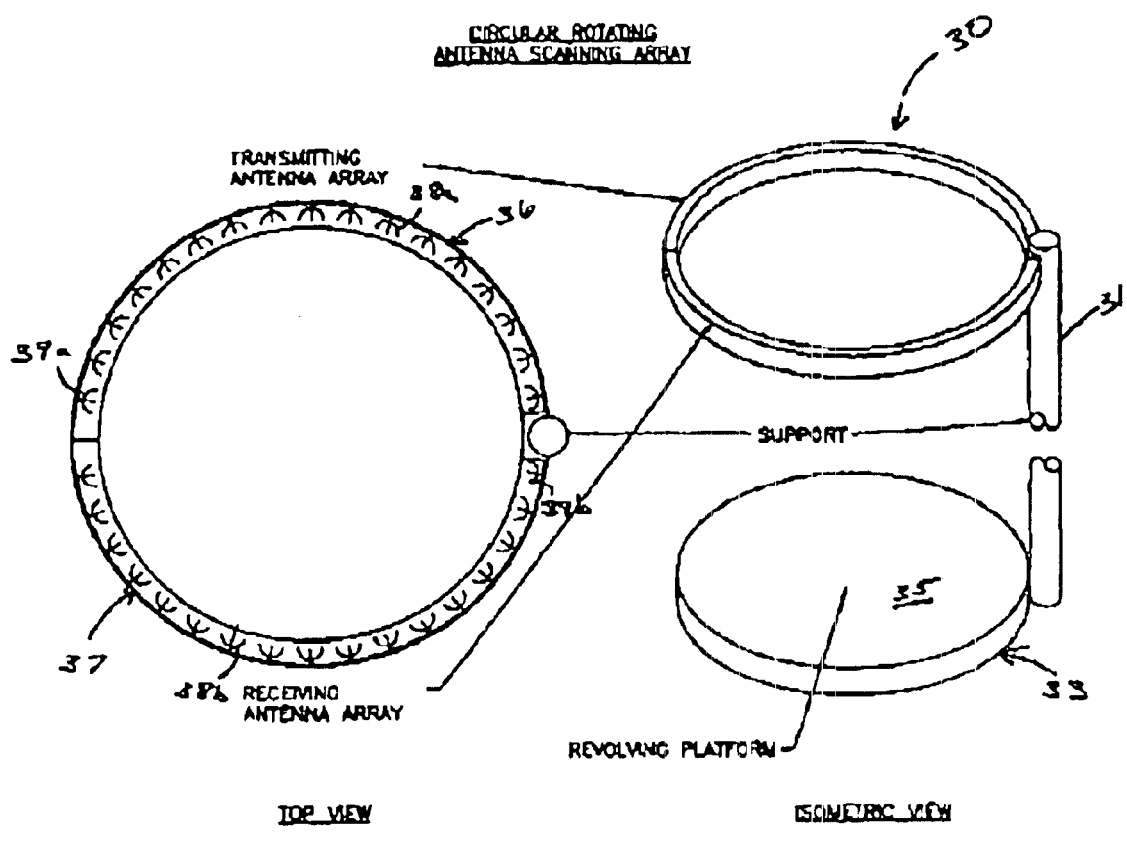
FIG. 3 is a perspective view of a circular antenna array, for describing an alternate embodiment of the invention.

In FIG. 3, an alternate embodiment of a scanning device according to the present invention is presented. Scanner 30 is disposed in a circular configuration supported by a support stanchion 31. A platform 33 with a top surface 35 is provided adjacent to the base of stanchion 31, and directly beneath scanner 30 on which an object, such as a human specimen, can stand. In operation, platform 33 can rotate about its center axis to provide a 360° presentation to scanner 30. Transmitting antenna array 36 presents a semicircular configuration array presenting a plurality of transmitting antennas, such as antenna 13 (FIG. 1). Receiving antenna array 37 also presents a semicircular configuration array presenting a plurality of transmitting antennas, such as 13 (FIG. 1). Each antenna in transmitting array 36 is focused to direct its energy output to a designated antenna in receiving array 37. For example, transmitting antenna 38a transmits to receiving antenna 38b; transmitting antenna 39a transmits to receiving antenna 39b, and so forth.

During operation of the specific embodiment of FIG. 3, scanner 30 is moved vertically along the entire height of an object being scanned, such as the human specimen 21 (FIG. 2) while such object is rotated on platform 33. The output of receiving array 37 is directed to a computer system that determines which antennas of such plurality of antennas, such as 13 (FIG. 1) in receiving array 37 receive energy from their corresponding transmitting antennas in transmitting array 36. Such computer system can develop a three-dimensional image of the object being scanned.

Figure 4:
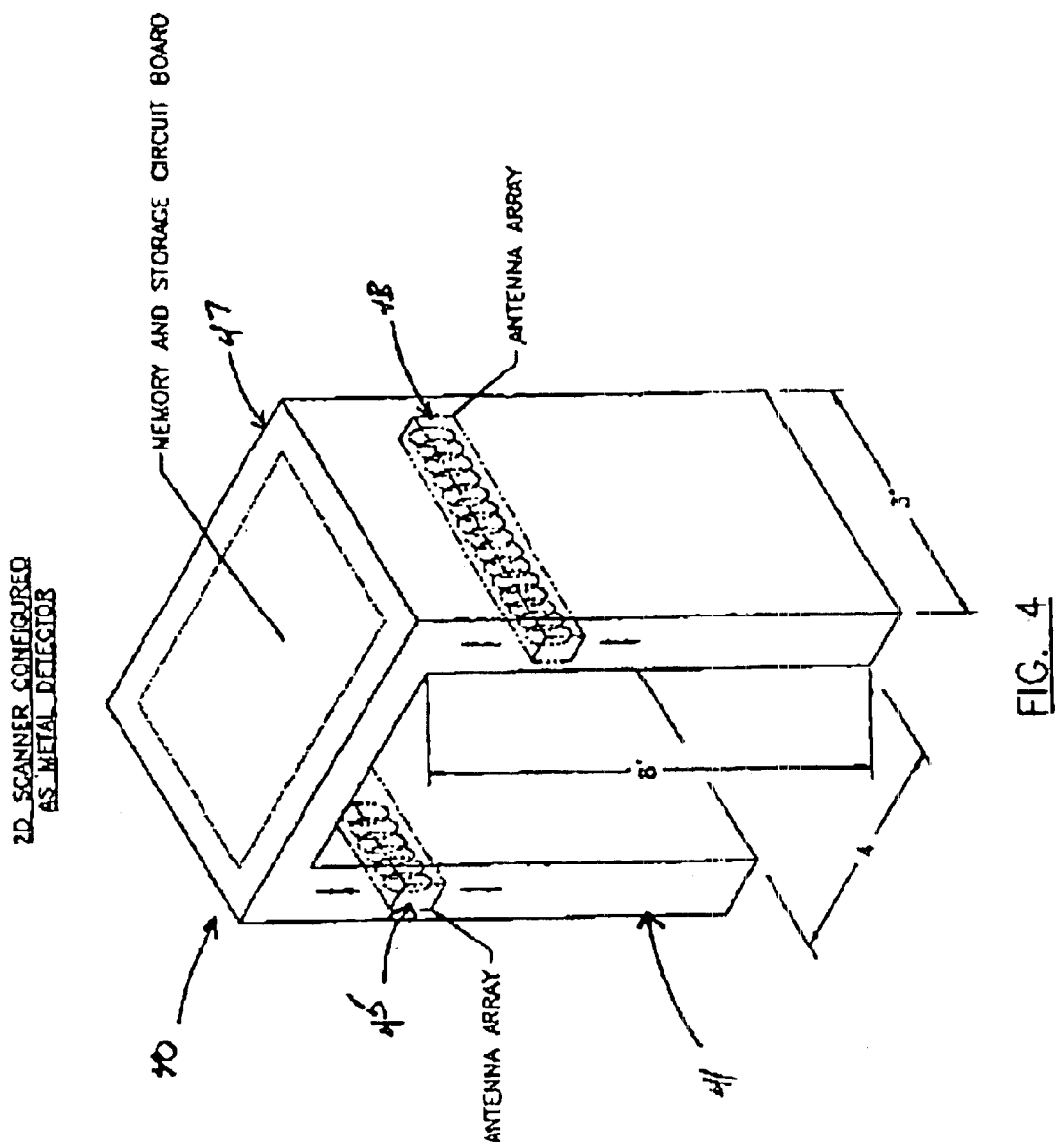
FIG. 4 is a perspective view of a horizontally oriented linear array, for describing a further embodiment of the invention.

Referring to FIG. 4, an alternate embodiment is illustrated depicting a two-dimensional scanner 40 configured similar to a metal detector. For security purposes, utilizing the present invention in a fixed array (similar to a metal detector), individuals can be scanned as they pass through a doorway or standing arch, such as 41 for access to a controlled area. In the illustrated embodiment, transmitting array 43 of scanner 40 is moved vertically along the entire height of the arch 41 substantially simultaneously with receiving array 45 to scan the entire body of a person standing within arch 41. A self-contained computer system disposed in the upper portion 47 of arch 41 receives the output of receiving array 45. Such computer system can develop a two-dimensional image of such person in scanner 40. Such computer system may also include a processor and memory in which is stored previously scanned images of individuals, some images of whom may be authorized to enter such controlled area. The processor compares the scanned image of the person standing within arch 41 with previously stored images and determines if the person is authorized to enter such controlled area. The computer system can signal for authorized and unauthorized individuals. The present invention therefore enables the control of access to secure areas, or any other control as desired.

Figure 5:
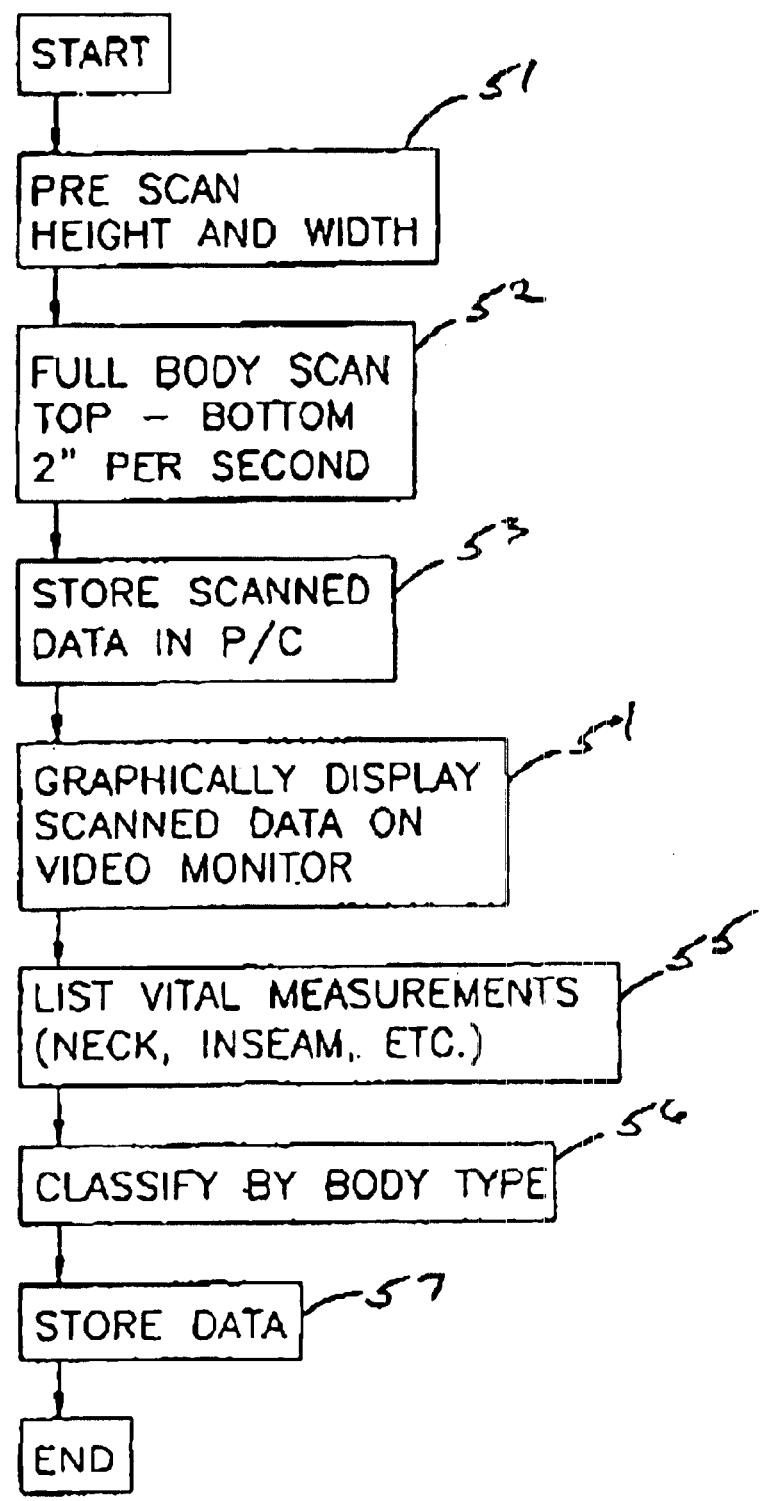
FIG. 5 is a flow chart, for describing operational steps carried out in the invention.

FIG. 5 is an illustration of a flow chart, for describing operational steps carried out in the invention. The first step, indicated at block 51 is to establish an approximate height and width of the object or person to be scanned. Such initial step establishes an outer limit for the scanner and ensures that a complete and accurate scan is obtained. In general, a full body scan can be performed from top to bottom as indicated at block 52, although a scan can be performed from bottom to top. In a preferred embodiment, the scanner (10 in FIGS. 1 and 2; 30 in FIG. 3; and 40 in FIG. 4) scans at a rate of about two inches per second. Other scanning rates may be used. The scanned data is stored 53 in a computer for further processing in accordance with the present invention. Some of such processing may include display of scanned data in a useful format, such as graphically 54 on a video monitor connected to such computer.

Figure 7:
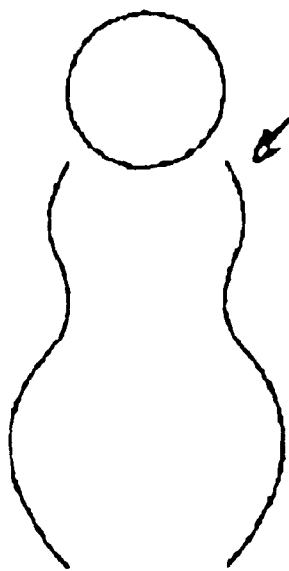
FIG. 7 is a representation of various body types.
Figure 7:
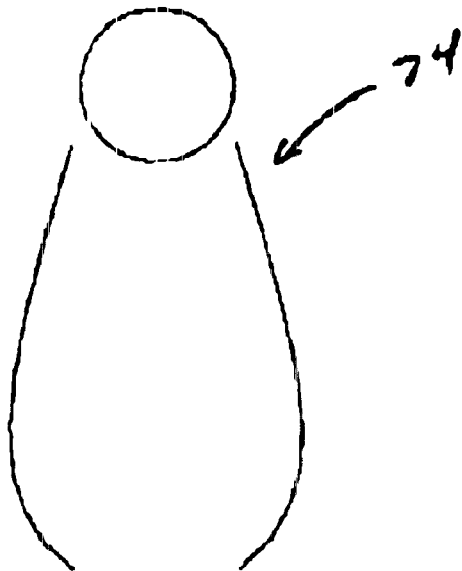
Figure 7:
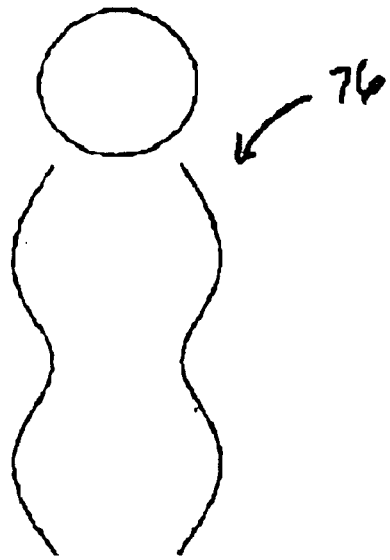
Figure 7:
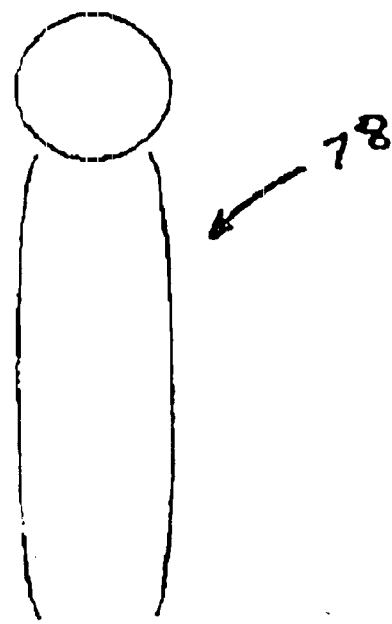

Processing of scanned data may also produce a list of vital measurements 55, such as described with reference FIG. 6. Body measurement processing can also preferably classify each measured body by type 56. Four representative body types are illustrated in FIG. 7. The final operational step is to store processed measurement data 57 for use by customers, clothing manufacturers, furniture designers, fitness equipment designers and the like.

FIG. 6 illustrates some of the information calculated and stored in a preferred embodiment of the present invention. Body measurements may be divided into categories, such as Category 1: Vitals 61; including one or more of the following items: body type, height, head size, neck, chest, waist, hips, inseam, sleeve, and the like. Another body measurement category may include Category 2: Profile 63; including one or more of the following items: body fat ratio, torso, leg, arm, hand, foot, face, and the like. Other data may also include profile rating and an identification number for future reference.

FIG. 7 shows a plurality of body types used for cataloguing. Body types are commonly characterized as pear shaped 72, wedge shaped 74, hourglass shaped 76 or stick shaped 78. Such characterization can be useful in designing clothing apparel.

Figure 8:
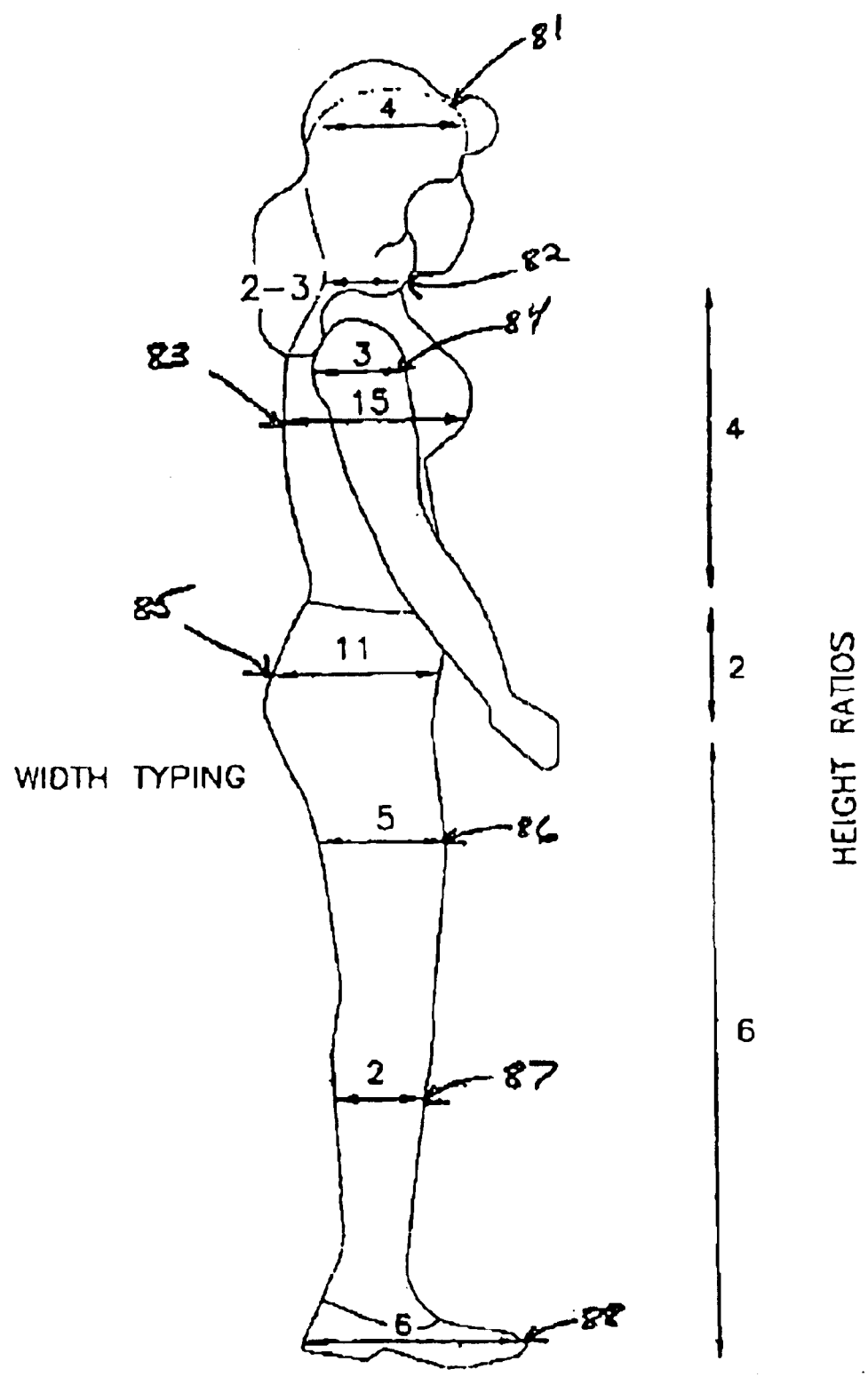
FIG. 8 is an elevational view of a human specimen, for describing dimension areas sampled by the invention.

FIG. 8 illustrates some of dimension areas sampled by the invention that are useful in establishing a profile of the subject being measured. Width typing in combination with height ratio profiling can be used for passive identification of an individual, such as when passing through a two dimensional scanner. By measuring several locations on a body, unique identification can be determined. For example, several body width measurements can be processed such as skull width 81, neck width 82, and torso width 83. Other dimensions can also be measured, such as shoulder width 84, hips 85, thighs 86, calf width 87 and foot length 88. Such measured dimensions can be compared in conjunction with height ratios, or body lengths, such as leg length, waist height, and torso length.

Figure 9:
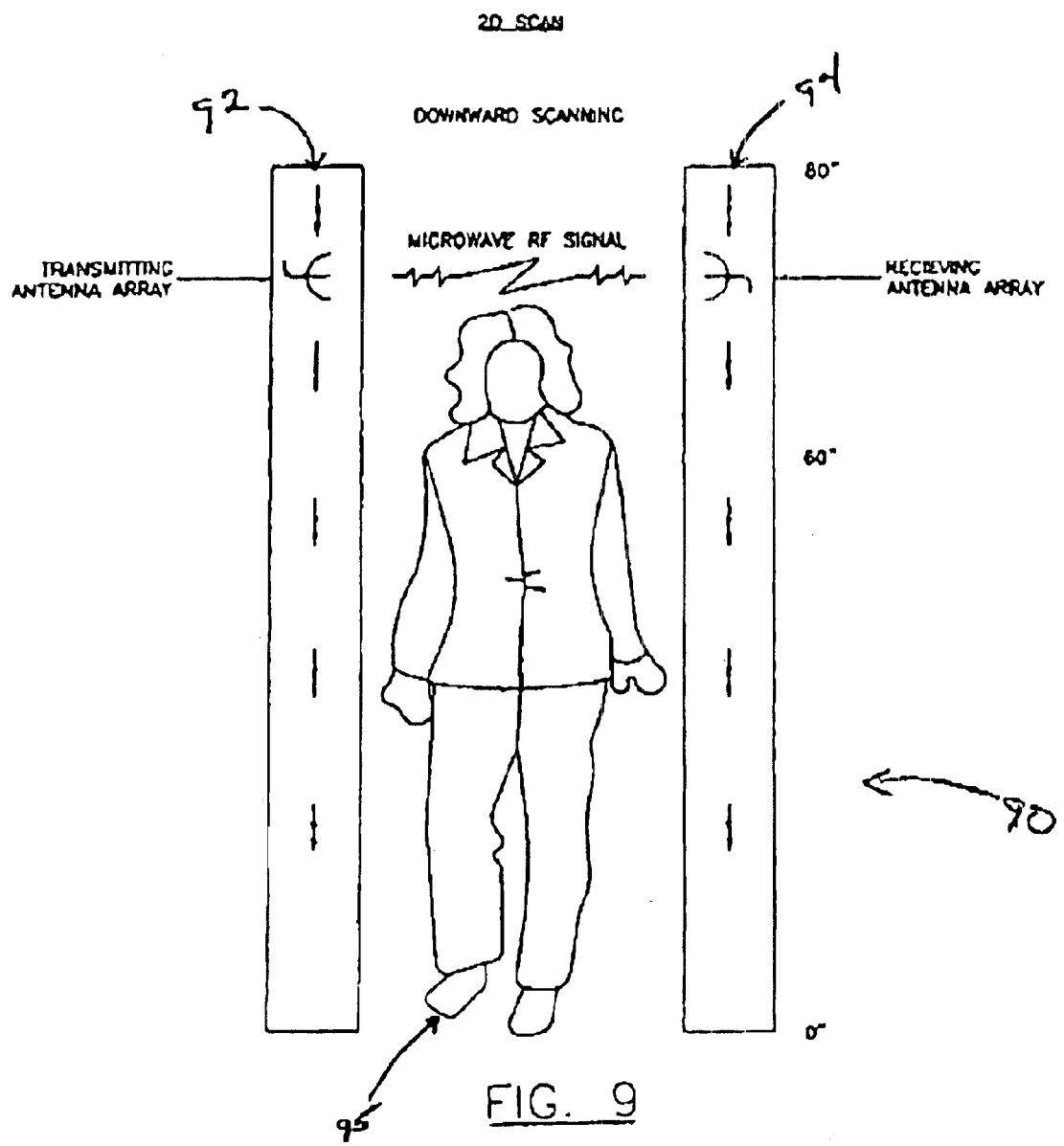
FIG. 9 is a schematic illustration of data capturing features of the invention, for describing operational steps of an alternate embodiment of the invention.

In practice, as illustrated in FIG. 9, a person 95 can walk through scanner 90 for two-dimensional scanning. Transmitting antenna array 92 radiates a microwave radio frequency signal to receiving antenna array 94. Not all transmitted energy will be received by receiving antenna array 94 due to such person 95 standing within the scanner 90. Transmitting antenna array 92 travels downward substantially simultaneously with receiving antenna array 94 to scan the full height of the person 95. A processing computer receives the output from receiving antenna array 94 and measures height and width profiles for the person 95. Such processing computer can provide an output for identification purposes or other use as appropriate. In a preferred embodiment, a two dimensional scanner can be used passively for access control to a secured area. For security purposes, utilizing the present invention in a fixed array, similar to an airport type metal detector, individuals can be scanned, with or without their prior knowledge, as they pass through a seemingly normal doorway, archway, or vertical pillars for identification purposes as well as for access screening for restricted areas, all without physical contact. The present invention appears to have widespread applications in law enforcement, security, clothing design and manufacture, as well as furniture design and health spa and physical fitness training.

Figure 10:
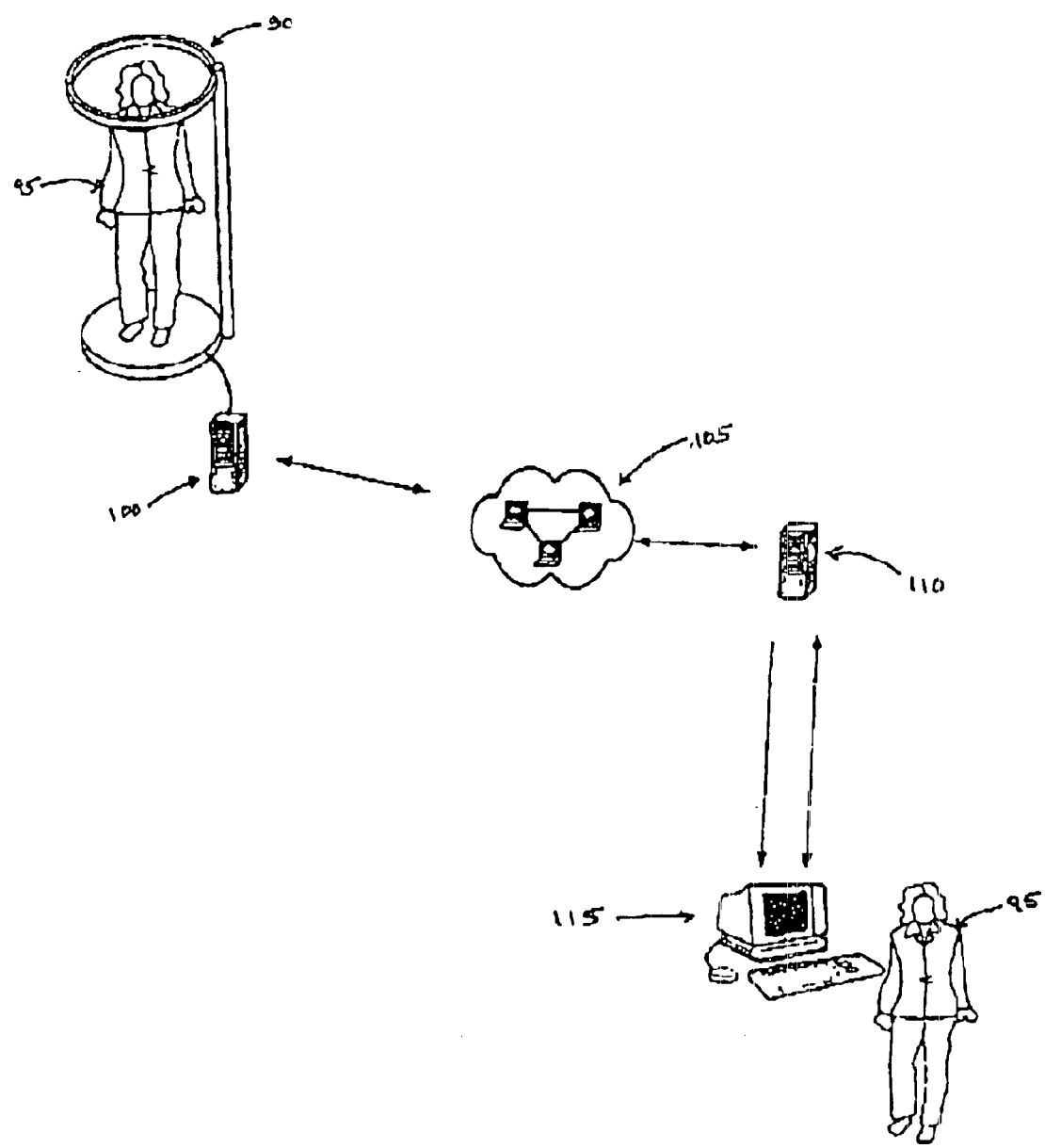
FIG. 10 is an illustration of an installation of a scanner and an integrated communication system consistent with the present invention.

FIG. 10 illustrates a scanner apparatus coupled to a communication system consistent with the present invention. Specifically, scanner 30 (FIG. 3) is readily available to person 95 (FIG. 9). Scanner 30 can operate to perform three-dimensional scanning of person 95. Processing computer 100 receives and processes signals generated by scanner 30 to provide functional information on person 95. Functional information is then communicated via computer network 105 to server 110. Person 95 can then access functional information through computer 115.

In an embodiment of the present invention, person 95 is provided an access code by processing computer 100 after operation of scanner 30. Functional information produced by processing computer 100 is relayed over a network 105; such as the Internet, a LAN network, a WAN network, or the like. Person 95 is preferably able to access functional information at home using computer 115, such as a PC computer or the like, by entering the assigned access code. The assigned access code is then transmitted to server 110 and upon verification, the server 110 obtains functional information for relay to person 95. Person 95 can then communicate the functional information to any merchandise provider for custom-fitted products.

While specific values, relationships, materials and steps have been set forth for purposes of describing concepts of the invention, it should be recognized that, in the light of the above teachings, those skilled in the art can modify those specifics without departing from basic concepts and operating principles of the invention taught herein. Therefore, for purposes of determining the scope of patent protection, reference shall be made to the appended claims in combination with the above detailed description.

What is claimed is:

1. An apparatus for measuring dimensions of a human being comprising:

a source of microwave signals having a predetermined amplitude and frequency, including an array of microwave radiating antennae, spaced from one another along a first direction;

at least one microwave receiver antenna which is located spaced from said radiating antennas, to receive radiated microwave signals that have passed through a space;

a processor that evaluates an output from said microwave receiver; and a movement part which moves said radiating antennas along a second direction which is substantially orthogonal to said first direction during a time of scanning, in which said processor calculates one or more of the following measurements of the human being's: (A) height; (B) head size; (C) neck; (D) chest; (E) waist; (F) hips; (G) inseam; and (K) sleeve.

2. The apparatus of claim 1, in which said radiating antennas are horizontally polarized.

3. The apparatus of claim 1, in which such said at least one of said radiating antennas or receiving antennas comprises an antenna array of a plurality of miniaturized antennas.

4. The apparatus of claim 3, in which each of said miniature antennas are horizontally polarized.

5. The apparatus of claim 1, wherein said radiating antennas are arranged along a circular configuration.

6. The apparatus of claim 1, wherein such processor means comprises a computer.

7. A method as in claim 1, wherein said processing evaluates the output from the microwave receiver to determine characteristics of a human located in said space, which has been scanned by said microwave signals, and to uniquely identify said human.

8. An apparatus for measuring dimensions of an object comprising:
   a source of microwave signals having a predetermined amplitude and frequency, including an array of microwave radiating antennae, spaced from one another along a first direction;
   at least one microwave receiver antenna which is located spaced from said radiating antennas, to receive radiated microwave signals that have passed through a space;
   a processor that evaluates an output from said microwave receiver; and
   a movement part which moves said radiating antennas along a second direction which is substantially orthogonal to said first direction during a time of scanning, further comprising (A) at least one server first computer unit; (B) a means for relaying said measured dimensions from said processor to said at least one server unit; and (C) a means second computer for relaying said measured dimensions from said at least one server unit to at least one user.

9. A method, comprising:
transmitting a microwave signal through a specified area through which a human subject is intended to pass;
determining locations where the microwave signal has been blocked by the human subject;
using said determined locations to uniquely identify an individual, wherein said using comprises obtaining at least one measurement value which is selected from the group consisting of the human being is: (A) height; (B) head size; (C) neck; (D) chest; (E) waist; (P) hips; (G) inseam; and (H) sleeve size.

* * * * *